United States Patent [19]

Dekeyser et al.

[11] Patent Number: 4,634,690

[45] Date of Patent: * Jan. 6, 1987

[54] SUBSTITUTED PYRIMIDINYL ORGANOPHOSPHORUS INSECTICIDES

[75] Inventors: Mark A. Dekeyser, Waterloo; Benjamin J. Pierce, Guelph, both of Canada; Richard C. Moore, Wallingford; Winchester L. Hubbard, Woodbridge, both of Conn.

[73] Assignees: Uniroyal Chemical Company, Inc., Middlebury, Conn.; Uniroyal, Ltd., Don Mills, Canada

[*] Notice: The portion of the term of this patent subsequent to Sep. 18, 2001 has been disclaimed.

[21] Appl. No.: 632,139

[22] Filed: Jul. 18, 1984

Related U.S. Application Data

[60] Continuation-in-part of Ser. No. 485,779, Apr. 18, 1983, Pat. No. 4,472,389, which is a division of Ser. No. 329,157, Dec. 10, 1981, Pat. No. 4,395,551.

[51] Int. Cl.$^4$ .................. A01N 57/16; C07F 9/65
[52] U.S. Cl. .......................... 514/81; 514/86; 544/243; 544/244
[58] Field of Search ............... 544/243, 244; 424/200; 514/80, 86, 81

[56] References Cited

U.S. PATENT DOCUMENTS

| | | | |
|---|---|---|---|
| 3,243,437 | 3/1966 | Sherlock | 544/243 |
| 3,857,838 | 12/1974 | Perronnet et al. | 544/243 |
| 3,904,624 | 9/1975 | Perronnet et al. | 544/243 |
| 4,152,426 | 5/1979 | Maurer et al. | 424/200 |
| 4,308,258 | 12/1981 | Okabe et al. | 424/200 |
| 4,395,551 | 7/1983 | Dekeyser et al. | 424/200 |
| 4,472,389 | 9/1984 | Dekeyser et al. | 424/200 |
| 4,584,295 | 4/1986 | Lüthy | 514/86 |

FOREIGN PATENT DOCUMENTS

| | | | |
|---|---|---|---|
| 0091700 | 10/1983 | European Pat. Off. | 544/243 |
| 0114045 | 7/1984 | European Pat. Off. | 544/243 |
| 0020756 | 2/1980 | Japan | 544/243 |

Primary Examiner—Nicholas S. Rizzo
Assistant Examiner—Diana G. Rivers
Attorney, Agent, or Firm—William E. Dickheiser

[57] ABSTRACT

An organophosphorus compound having the structural formula

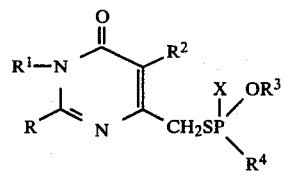

where R is $C_1$–$C_4$ alkyl; $R^1$ is hydrogen or methyl; or R and $R^1$ together are a diradical having the formula —SC(Y)=Z—, where Y is halogen, hydrogen or $C_1$–$C_2$ alkyl; and Z is nitrogen, CH, C(CH$_3$) or C(C$_2$H$_5$) with the proviso that if Y is hydrogen, Z cannot be CH; $R^2$ is hydrogen, chlorine or bromine; $R^3$ is methyl or ethyl; $R^4$ is methoxy, ethoxy, —SCH$_3$ or —SC$_2$H$_5$; and X is oxygen or sulfur and their hydrochlorides is disclosed. These compounds are useful as insecticides or nematocides.

In another aspect of this invention a method of controlling rice planthoppers is provided. In this method an insecticidally effective amount of a compound having the formula given above where R is $C_1$–$C_4$ alkyl or benzyl; $R^1$ is hydrogen or $C_1$–$C_3$ alkyl; or R and $R^1$ together are a diradical selected from the group consisting of —CH=CH—CH=CH—, —CH=CCl—CH=CH—, —CH=C(CH$_3$)—CH=CH— and —SC(Y)=Z—, where Y is halogen, hydrogen or $C_1$–$C_2$ alkyl; and Z is nitrogen, CH, C(CH$_3$) or C(C$_2$H$_5$); $R^2$ is hydrogen or bromine; $R^3$ is methyl or ethyl; $R^4$ is methoxy, ethoxy or propylthio, with the proviso that if $R^2$ is bromine, $R^4$ is propylthio, and X is oxygen or sulfur is applied to the loci where rice planthoppers reside.

5 Claims, No Drawings

SUBSTITUTED PYRIMIDINYL ORGANOPHOSPHORUS INSECTICIDES

REFERENCE TO RELATED APPLICATIONS

This is a continuation-in-part application of U.S. patent application, Ser. No. 485,779 filed Apr. 18, 1983, now U.S. Pat. No. 4,472,389, which is a division of U.S. patent application, Ser. No. 329,157 filed Dec. 10, 1981 now U.S. Pat. No. 4,395,551.

This invention relates to new organophosphorus compounds and insecticidal compositions containing such compounds, as well as to a method of controlling insects by application of such compositions. The invention further relates to new chemical intermediates useful in making said compounds.

The following references are of interest:
U.S. Pat. No. 4,042,765, Floyd et al, Aug. 16, 1977.
Swiss Pat. No. 524,617, Lonza AG, Aug. 15, 1972.
Abstract 18253U C of Belgian Pat. No. 788,828, Roussel, Sept. 16, 1971.
Abstract 18874U C of German Pat. No. 224,363, Squibb, Sept. 17, 1971.
Abstract 40370V/22 of French Pat. No. 2,197,513, Roussel, Sept. 16, 1971.
Abstract 50790 D/28 of Japanese Pat. No. 137,927, Sumitomo Chemical, Oct. 24, 1979.
Boehme & Weisel, "Beta-Substituted Enamine", Arch. Pharm., 310, pp. 26–29 (1977).

In one aspect, the invention relates to
(A) new insecticidal organophosphorus compounds of the formula

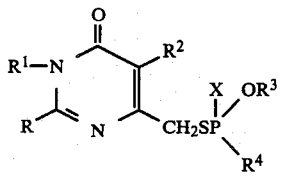

wherein R is $C_1$–$C_3$ alkyl or phenyl, $R^1$ is hydrogen or R and $R^1$ together form a 1,3-butadien-1,4-diyl group optionally substituted with a methyl or chloro group, or R and $R^1$ together form a 1,2-ethenediylthio group wherein sulfur is attached to carbon; $R^2$ is hydrogen or halogen, X is O or S, $R^3$ is $C_1$–$C_3$ alkyl; and $R^4$ is $C_1$–$C_3$ alkoxy or propylthio and their hydrochlorides with the proviso that if R is phenyl, $R^3$ is methyl and $R^4$ is methoxy.

In another aspect the invention relates to
(B) new chemical intermediates of the formula

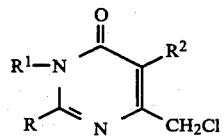

wherein R and $R^1$ together form a 1,3-butadien-1,4-diyl group optionally substituted with a methyl or chloro group, or R and $R^1$ together form a 1,2-ethenediylthio group wherein sulfur is attached to carbon, and $R^2$ is halogen.

Preferred compounds of the invention are those of formulas I and II above wherein R and $R^1$ together form a 1,3-butadien-1,4-diyl group optionally substituted with a chloro group, or R and $R^1$ together form a 1,2-ethenediylthio group wherein sulfur is attached to carbon, $R^2$ is hydrogen or halogen (chlorine, bromine), X is O or S, $R^3$ is $C_1$ or $C_2$ alkyl, and $R^4$ is $C_1$- or $C_2$ alkoxy or propylthio.

Representative examples of such formula I compounds are:
O,O-dimethyl S-[(4-oxo-4H-pyrido[1,2-a]pyrimidin-2-yl)methyl]phosphorodithioate
O,O-dimethyl S-[(5-oxo-5H-thiazolo[3,2-a]pyrimidin-7-yl)methyl]phosphorodithioate
S-[(3,4-dihydro-2-(1-methylethyl)-4-oxo-6-pyrimidinyl)methyl]O,O-dimethyl phosphorodithioate In another aspect of this invention a compound having the structural formula I, useful in the control of insects and nematodes, is provided. These compounds are those in which R is $C_1$–$C_4$ alkyl; $R^1$ is hydrogen or methyl; or R and $R^1$ together are a diradical having the formula —SC(Y)=Z—, where Y is halogen, hydrogen or $C_1$–$C_2$ alkyl; and Z is nitrogen, CH, C(CH$_3$) or C(C$_2$H$_5$) with the proviso that if Y is hydrogen Z cannot be CH; $R^2$ is hydrogen, chlorine or bromine; $R^3$ is methyl or ethyl; $R^4$ is methoxy, ethoxy, —SCH$_3$ or —SC$_2$H$_5$; and X is oxygen or sulfur. The hydrochloride salt of these compounds is also within the contemplation of this invention. These compounds have utility in the control of insects and nematodes.

More preferably, the compuonds of this aspect of the invention have the structural formula I where R is $C_1$–$C_3$ alkyl; Y is Cl, Br, hydrogen, $C_1$–$C_2$ akyl with the proviso that Z is not CH if Y is hydrogen; and $R^4$ is methoxy or ethoxy.

A still another aspect of this invention is directed to a method for controlling rice planthoppers. In this method control is obtained by applying an insecticidally effective amount, to the loci where rice planthoppers reside of a compound having the structural formula I where R is $C_1$–$C_4$ alkyl or benzyl; $R^1$ is hydrogen or $C_1$–$C_3$ alkyl; or R and $R^1$ together form a diradical selected from the group consisting of —CH=CH—CH=CH—, —CH=CCl—CH=CH—, —CH=C(CH$_3$)—CH=CH— and —SC(Y)=Z— where Y is halogen, hydrogen or $C_1$–$C_2$ alkyl; and Z is nitrogen, CH, C(CH$_3$) or C(C$_2$H$_5$); $R^2$ is hydrogen or bromine; $R^3$ is methyl or ethyl; $R^4$ is methoxy, ethoxy or propylthio, with the proviso that if $R^2$ is bromine, $R^4$ is propylthio; and Xi is oxygen or sulfur.

Insecticidal compounds (I) of this invention may be made by reacting a chloromethyl pyrimidine derivative II with a thio- or dithiophosphate. The reaction proceeds according to the following equation:

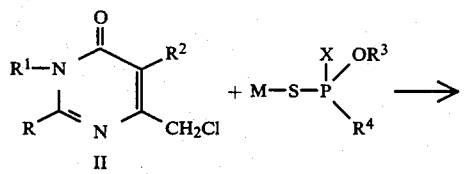

-continued

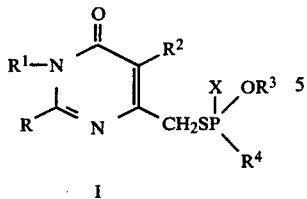

wherein M is an alkali metal or ammonium cation. This reaction may be carried out in alcohol or a mixture of alcohol and toluene, at temperatures normally ranging from 50°-100° C. The pressure normally is atmospheric. The reaction will usually be complete within 2 to 10 hours. Yields are 80-95%. The intermediate chloromethyl pyrimidine derivatives (II) in the above equation may be prepared by reacting ethyl 4-chloroacetoacetate with a 2-pyridinamine or 2-thiazolamine or an imidamide, which may be followed by a halogenation step with N-halosuccinimide. The reaction proceeds according to the equation:

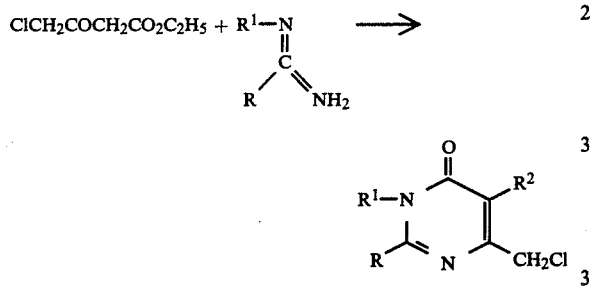

wherein $R^1$ and R are as previously described. This reaction is normally carried out in polyphosphoric acid or alcohol, at temperatures of 0°-140° C. for a period of ½ to 12 hours.

The following examples serve to illustrate the practice of the invention in more detail. All temperatures are in degree Celsius. The terms NMR and IR stand for nuclear magnetic resonance and infra red, respectively.

EXAMPLE 1

O,O-Diethyl S-[(4-oxo-4H-pyrido[1,2-a]pyrimidin-2-yl)methyl]phosphorodithioate 37.7 g 2-pyridinamine was dissolved in about 250 g polyphosphoric acid, at 40°-50°, using a mechanically driven stirrer. To this mixture was added, dropwise, 54 ml ethyl 4-chloroacetoacetate. After the addition, the mixture was heated to about 125° for ½ hour. After cooling to about 50°, the mixture was poured into 1500 ml of ice water, and the mixture was extracted with an equal volume of chloroform. After drying and evaporation of chloroform, about 45 g 2-(chloromethyl)-4H-pyrido[1,2-a]pyrimidin-4-one (m.p. 171°-174°) was obtained.

The chloromethyl compound (5 g) and 100 ml of toluene were mixed and heated to about 60°. To this mixture was added, dropwise, a mixture of 5 g O,O-diethyl phosphorodithioate and 1.68 g potassium hydroxide dissolved in 50 ml absolute ethanol. After the addition, the mixture was heated at 60°-70° for 4 hours, filtered and evaporated; yield 7.9 of an oil.

Analysis for $C_{13}H_{17}N_2O_3PS_2$: CALCULATED: C, 45.34; H, 4.97; N, 8.13. FOUND: C, 44.09; H, 5.18; N, 8.30.

EXAMPLE 2

6-Chloro-7-(chloromethyl)-5H-thiazolo[3,2-a]pyrimidin-5-one

The intermediate 7-(chloromethyl)-5H-thiazolo[3,2-a]pyrimidin-5-one was prepared from 2-thiazolamine and ethyl 4-chloroacetoacetate by the procedure described in EXAMPLE 1. The m.p. was 132°-136° C., and the structure was confirmed by NMR and IR.

The chloromethyl intermediate (17 g) was stirred with 150 ml of carbon tetrachloride, 15 g of N-chlorosuccinimide and 250 ml of ethyl acetate. The mixture was then heated at 60°-65° for 4 hours and the solvent evaporated off under reduced pressure. The solid residue was washed with hot water and filtered. The solid, m.p. 157°-165°, weighed 9 g.

Analysis for $C_7H_4Cl_2N_2OS$: CALCULATED: C, 35.95; H, 1.75; N, 11.82. FOUND: C, 35.76; H, 1.71; N, 11.91.

EXAMPLE 3

S-[(6-Chloro-5-oxo-5H-thiazolo[3,2-a]pyrimidin-7-yl)methyl]O,O-dimethyl phosphorodithioate The compound of EXAMPLE 2 (7 g) and 100 ml of toluene was stirred and heated to 70°. To this mixture was added, dropwise, a solution of 14 g ammonium dimethyl phosphorodithioate in 200 ml methanol. The resulting mixture was kept at 70° for 6 hours, then the methanol was distilled off. Toluene (400 ml) was added, and the mixture was washed with water, separated, dried and evaporated under reduced pressure. The solid which remained was washed with toluene and filtered. The solid, m.p. 125°-130°, weighed 2.5 g.

Analysis for $C_9H_{10}ClN_2O_3PS_3$: CALCULATED: C, 31.28; H, 3.12; N, 8.10. FOUND: C, 30.23; H, 3.26; N, 8.11.

EXAMPLE 4

S-[(3,4-Dihydro-2-(1-methylethyl)-4-oxo-6-pyrimidinyl)methyl]O,O-dimethyl phosphorodithioate The intermediate, 6-(chloromethyl)-2-(1-methylethyl)-4(1H)-pyrimidinone, was prepared according to Swiss Pat. No. 524617 from ethyl 4-chloroacetoacetate and isobutyramidine. m.p. 123°-125°. The intermediate chloromethyl compound (25 g) was stirred with 50 ml methanol at room temperature. To this mixture was added, dropwise, a solution of 25 g ammonium dimethyl phosphorodithioate dissolved in 500 ml methanol. The mixture was then heated to reflux for 6 hours, then the solvent was evaporated under reduced pressure yielding a solid. The solid was dissolved in dichloromethane and washed with water, separated, dried, and the solvent was evaporated. The remaining solid was recrystallized from toluene; yield: 15.9 g, m.p. 89°-93°.

Analysis for $C_{10}H_{17}N_2O_3PS_2$: CALCULATED: C, 38.94; H, 5.55; N, 9.08. FOUND: C, 38.54; H, 5.77; N, 9.36.

TABLE I lists further intermediates prepared in a similar manner, and TABLE II lists further organophosphorus compounds essentially prepared according to the procedures of the the previous examples. It should be noted that the intermediates in some instances also exhibited insecticidal or nematocidal activity such as Examples 2, 5, 6, 8, 9, 10, 11 and 12.

TABLE I

Chloromethyl Pyrimidinone Derivatives

| EXAMPLE | NAME | M.P. °C. | ANALYSIS CALC/FOUND | | | IR | MNR |
|---|---|---|---|---|---|---|---|
| | | | C | H | N | | |
| 5 | 3-bromo-2-(chloromethyl)-4H—pyrido[1,2-a]pyrimidin-4-one | 197–200 | 39.51 / 39.69 | 2.21 / 2.36 | 10.23 / 10.24 | X | X |
| 6 | 6-chloro-2-(chloromethyl)-4H—pyrido[1,2-a]pyrimidin-4-one | 149–151 | 47.18 / 47.05 | 2.64 / 3.03 | 12.22 / 12.23 | X | X |
| 7 | 3-chloro-2-(chloromethyl)-4H—pyrido[1,2-a]pyrimidin-4-one | 170–173 | 47.18 / 46.83 | 2.64 / 2.80 | 12.22 / 12.03 | X | X |
| 8 | 3,6-dichloro-2-(chloromethyl)-4H—pyrido[1,2-a]pyrimidin-4-one | 197–203 | 41.01 / 40.83 | 1.91 / 2.14 | 10.62 / 10.70 | X | X |
| 9 | 2-(chloromethyl)-5-methyl-4H—pyrido[1,2-a]pyrimidin-4-one | 119–120 | 57.70 / 57.76 | 4.64 / 4.44 | 13.37 / 13.46 | X | X |
| 10 | 2-(chloromethyl)-7-methyl-4H—pyrido[1,2-a]pyrimidin-4-one | 110–111 | 57.70 / 57.81 | 4.64 / 4.45 | 13.37 / 13.36 | X | X |
| 11 | 6-bromo-7-(chloromethyl)-5H—thiazolo[3,2-a]pyrimidin-5-one | 187–193 | 30.07 / 30.04 | 1.44 / 1.41 | 10.01 / 10.04 | X | X |
| 12 | 3-bromo-6-chloro-2-(chloromethyl)-4H—pyrido[1,2-a]pyrimidin-4-one | 193–196 | 35.09 / 34.72 | 1.63 / 1.74 | 9.09 / 9.47 | X | X |

TABLE II

Substituted Pyrimidinyl Phosphorus Compounds

| EXAMPLE | NAME | M.P. °C. | ANALYSIS CALC/FOUND | | | IR | MNR |
|---|---|---|---|---|---|---|---|
| | | | C | H | N | | |
| 13 | Hydrochloride of (16) | 139–142 | 34.14 / 34.16 | 4.16 / 4.34 | 7.23 / 7.23 | X | X |
| 14 | O,O—bis(1-methylethyl) S—[(4-oxo-4H—pyrido[1,2-a]pyrimidin-2-yl)methyl] phosphorodithioate | 71–55 | 48.37 / 47.84 | 5.68 / 5.16 | 7.52 / 7.87 | X | X |
| 15 | O,O—diethyl S—[(4-oxo-4H—pyrido[1,2-a]pyrimidin-2-yl)methyl] phosphorothioate | oil | 47.55 / 45.90 | 5.21 / 5.21 | 8.52 / 7.88 | | X |
| 16 | O,O—diethyl S—[(5-oxo-5H—thiazolo[3,2-a]pyrimidin-7-yl)methyl] phosphorodithioate | oil | 37.70 / 37.56 | 4.31 / 4.30 | 7.99 / 7.73 | | X |
| 17 | O,O—diethyl S—[(5-oxo-5H—thiazolo[3,2-a]pyrimidin-7-yl)methyl] phosphorothioate | oil | 39.51 / 37.44 | 4.52 / 4.53 | 8.37 / 7.96 | | X |
| 18 | O,O—dimethyl S—[(7-methyl-4-oxo-4H—pyrido[1,2-a]pyrimidin-2-yl)methyl] phosphorodithioate | 94–97 | 43.62 / 43.58 | 4.57 / 4.50 | 8.47 / 8.38 | X | X |
| 19 | O,O—diethyl S—[(7-methyl-4-oxo-4H—pyrido[1,2-a]pyrimidin-2-yl)methyl] phosphorodithioate | 45–48 | 46.91 / 46.31 | 5.34 / 5.49 | 7.81 / 7.43 | X | X |
| 20 | O,O—dimethyl S—[(5-methyl-4-oxo-4H—pyrido[1,2-a]pyrimidin-2-yl)methyl] phosphorodithioate | 75–76 | 43.62 / 40.76 | 4.57 / 4.59 | 8.47 / 7.51 | X | X |
| 21 | O,O—diethyl S—[(5-methyl-4-oxo-4H—pyrido[1,2-a] pyrimidin-2-yl)methyl] phosphorodithioate | oil | 46.91 / 44.20 | 5.34 / 5.39 | 7.81 / 7.58 | X | X |
| 22 | S—[(3,4-dihydro-4-oxo-2-phenyl-6-pyrimidinyl)methyl] O,O—dimethylphosphorodithioate | 102–106 | 45.60 / 44.90 | 4.41 / 4.34 | 8.17 / 8.23 | X | X |
| 23 | S—[(3,4-dihydro-2-methyl-4-oxo-6-pyrimidinyl)methyl] O,O—dimethylphosphorodithioate | 92–97 | 34.27 / 34.20 | 4.67 / 4.67 | 9.98 / 9.68 | X | X |

TABLE II-continued
Substituted Pyrimidinyl Phosphorus Compounds

| EXAMPLE | NAME | M.P. °C. | ANALYSIS CALC/FOUND C | H | N | IR | MNR |
|---|---|---|---|---|---|---|---|
| 24 | S—[(3,4-dihydro-2-methyl-4-oxo-6-pyrimidinyl)methyl] O,O—diethylphosphorodithioate | 83–86 | 38.94 / 38.94 | 5.55 / 5.56 | 9.08 / 8.66 | X | X |
| 25 | O,O—dimethyl S—[(4-oxo-4H—pyrido-[(1,2-a]pyrimidin-2-yl)methyl] phosphorodithioate | 69–70 | 41.76 / 41.47 | 4.14 / 4.44 | 8.85 / 8.46 | X | X |
| 26 | S—[(3,4-dihydro-2-(1-methylethyl)-4-oxo-6-pyrimidinyl)methyl O,O—diethyl phosphorodithioate | 74–76 | 42.84 / 42.95 | 6.29 / 6.04 | 8.32 / 9.04 | X | X |
| 27 | S—[(3-bromo-7-methyl-4-oxo-4H—pyrido[1,2-a]pyrimidin-2-yl)methyl] O,O—diethyl phosphorodithioate | 100–104 | 38.44 / 37.60 | 4.14 / 4.21 | 6.40 / 7.06 | X | X |
| 28 | S—[(3-bromo-4-oxo-4H—pyrido-[1,2-a]pyrimidin-2-yl)methyl] O,O—diethyl phosphorodithioate | 68–72 | 36.88 / 36.99 | 3.81 / 3.84 | 6.61 / 7.11 |  | X |
| 29 | S—[(6-chloro-4-oxo-4H—pyrido-[1,2-a]pyrimidin-2-yl)methyl] O,O—dimethyl phosphorodithioate | 88–90 | 37.66 / 37.08 | 3.44 / 3.45 | 7.98 / 7.80 | X | X |
| 30 | S—[(6-chloro-4-oxo-4H—pyrido-[1,2-a]pyrimidin-2-yl)methyl] O,O—diethyl phosphorodithioate | 72–76 | 41.22 / 40.41 | 4.23 / 4.37 | 7.40 / 7.25 | X | X |
| 31 | Hydrochloride of (30) | 132–135 | 37.59 / 38.50 | 4.09 / 3.99 | 6.74 / 6.92 | X | X |
| 32 | S—[(3-bromo-4-oxo-4H—pyrido-[1,2-a]pyrimidin-2-yl)methyl] O,O—dimethyl phosphorodithioate | 123–126 | 33.35 / 33.30 | 3.27 / 3.07 | 7.07 / 7.15 |  | X |
| 33 | O,O—dimethyl S—[(5-oxo-5H—thiazolo[3,2-a]pyrimidin-7-yl)methyl] phosphorodithioate | oil | 33.53 / 33.37 | 3.43 / 3.68 | 8.68 / 8.98 | X | X |
| 34 | S—[(3-bromo-6-chloro-4-oxo-4H—pyrido[1,2-a]pyrimidin-2-yl)methyl] O,O—dimethyl phosphorodithioate | 138–141 | 30.74 / 28.97 | 2.58 / 2.63 | 6.51 / 7.09 | X | X |
| 35 | S—[(3,6-dichloro-4-oxo-4H—pyrido[1,2-a]pyrimidin-2-yl)methyl] O,O—dimethyl phosphorodithioate | 130–132 | 34.29 / 34.68 | 2.87 / 3.00 | 7.26 / 7.75 | X | X |
| 36 | S—[(3-bromo-6-chloro-4-oxo-4H—pyrido[1,2-a]pyrimidin-2-yl)methyl] O,O—diethyl phosphorodithioate | 128–132 |  |  |  |  | X |
| 37 | S—[(3-chloro-4-oxo-4H—pyrido-[1,2-a]pyrimidin-2-yl)methyl] O,O—dimethyl phosphorodithioate | 105–110 | 37.55 / 36.31 | 3.43 / 3.65 | 7.95 / 8.10 | X | X |
| 38 | S—[(6-bromo-5-oxo-5H—thiazolo-[3,2-a]pyrimidin-7-yl)methyl] O,O—dimethyl phosphorodithioate | 121–124 | 26.93 / 26.58 | 2.51 / 2.54 | 6.97 / 6.41 | X | X |
| 39 | O,O—diethyl S—[(4-oxo-4H—pyrido-[1,2-a]pyrimidin-2-yl)methyl] phosphorodithioate hydrochloride | 125–130 | 40.99 / 41.27 | 4.76 / 4.98 | 7.35 / 6.94 | X | X |
| 40 | O—ethyl S—[(5-oxo-5H—thiazolo-[3,2-a]pyrimidin-7-yl)methyl] S—propyl phosphorodithioate | oil | 39.54 / 39.19 | 4.70 / 4.70 | 7.68 / 7.82 | X | X |
| 41 | S—[(3-bromo-4-oxo-4H—pyrido-[1,2-a]pyrimidin-2-yl)methyl] O—ethyl S—propyl phosphoro- | oil |  |  |  |  | X |

TABLE II-continued

Substituted Pyrimidinyl Phosphorus Compounds

| EXAMPLE | NAME | M.P. °C. | ANALYSIS CALC/FOUND | | | IR | MNR |
|---|---|---|---|---|---|---|---|
| | | | C | H | N | | |
| | dithioate | | | | | | |

Additional organophosphorus compounds prepared essentially in accordance with the procedures of the previous examples are summarized in TABLE III.

TABLE III

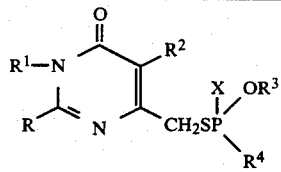

| Example No. | R | $R^1$ | $R^2$ | $R^3$ | $R^4$ | X | m.p. °C. |
|---|---|---|---|---|---|---|---|
| 44 | —SC(Br)=CH— | | H | $C_2H_5$ | $OC_2H_5$ | S | |
| 45 | HCl salt of the compound of Ex. 44 | | | | | | |
| 46 | —SC($CH_3$)=C($CH_3$)— | | H | $C_2H_5$ | $OC_2H_5$ | S | |
| 47 | HCl salt of the compound of Ex. 46 | | | | | | |
| 48 | $CH_3$ | $CH_3$ | H | $C_2H_5$ | $OC_2H_5$ | S | |
| 49 | HCl salt of the compound of Ex. 48 | | | | | | |
| 50 | —SCH=N— | | H | $C_2H_5$ | $OC_2H_5$ | S | |
| 51 | HCl salt of the compound of Ex. 50 | | | | | | |
| 52 | —SC($CH_3$)=N— | | H | $CH_3$ | $OCH_3$ | S | |
| 53 | HCl salt of the compound of Ex. 52 | | | | | | |
| 54 | —SCH=N— | | Cl | $C_2H_5$ | $OC_2H_5$ | S | |
| 55 | —SCH=N— | | Cl | $CH_3$ | $OCH_3$ | S | |
| 56 | HCl salt of the compound of Ex. 24 | | | | | | |
| 57 | =SCH($C_2H_5$)=N— | | H | $C_2H_5$ | $OC_2H_5$ | S | |

Application of the organophosphorus compounds of this invention as insecticides, nematocides and acaricides can be carried out in a number of ways. For practical applications, the compounds can be used alone, or dissolved or suspended in suitable carriers such as water, alcohols, ketones, phenols, toluene or xylenes. Optionally, one or more suface active agents and/or inert diluents can be added to the formulation to facilitate handling. The formulations can take the form of dusts, granules, wettable powders, pastes, emulsifiable concentrates, or water soluble solids.

For example, the pesticidal compounds of this invention can be applied as dusts when admixed with or absorbed on powdered solid carriers, such as the various mineral silicates, e.g., mica, talc pyrophyllite and clays, or as liquids or sprays when in a liquid carrier, as in solution in a suitable solvent such as acetone, benzene or kerosene, or dispersed in a suitable non-solvent medium, for example, water. In protecting plants (the term includes plant parts,) the chemicals are preferably applied as aqueous emulsions containing a surface-active dispersing agent which may be an anionic, nonionic or cationic surface-active agent. Such surface-active agents are well known and reference is made to U.S. Pat. No. 2,547,724, columns 3 and 4, for detailed examples of the same. The chemicals may be mixed with such surface-active dispersing agents, with or without an organic solvent, as concentrates for subsequent addition of water to make aqueous suspensions of the chemicals of the desired concentration. The chemicals may be admixed with powdered solid carriers, such as mineral silicates together with a surface-active dispersing agent so that a wettable powder is obtained which may then be applied directly to loci to be protected, or may be shaken with water to form a suspension of the chemical (and powdered solid carrier) in water for application in that form. Granular formulations of these chemicals are prepared using a granular or pelletized form of carrier such as granular clays, vermiculite, charcoal or corn cobs. The formulations are then applied by broadcasting, side dressing, soil incorporation or seed treatment. The chemicals may be applied to loci to be protected by the aerosol method. Solutions for aerosol treatment may be prepared by dissolving the chemical directly in the aerosol carrier which is liquid under pressure but which is a gas at ordinary temperature (e.g., 20° C.) and atmospheric pressure, or the aerosol solution may be prepared by first dissolving the chemical in a less volatile solvent and then admixing such solution with the highly volatile liquid aerosol carrier. The chemicals may be used admixed with carriers that are active themselves, for example: insecticides, acaricides, fungicides, or bactericides.

The pesticidal formulations of the invention will contain amounts of the compounds effective for the particular method of control. These amounts can vary widely; typically, the range is from 0.1 to 95% active ingredient. Spray dilutions can contain from a few parts per million to full strength concentrates applied by ultra low volume techniques. Concentrations per unit area, where plants are the area treated, can vary from 0.01 to 50 pounds per acre, and preferably from 0.1 to 10 pounds per acre.

To control pests, sprays of the compounds may be applied to the pests directly, to plants upon which they feed, or both. Another effective method of attack involves application of the compounds to the soil or other medium in which insects live.

Harmful insects, nematodes and arachnids attack a wide variety of plants, including both ornamental and agricultural plants plants and inflict damage by consuming foliage, withdrawing vital juices from the plants, secreting toxins and often by transmitting diseases. The compounds utilized in this invention can prevent such damage. The methods of application, and the selection and concentration of these compounds will, of course, vary depending upon such circumstances as area, climate, plant tolerance, etc. One skilled in the art can select the proper approach by simple experiments.

The compounds of this invention are especially useful as insecticides and nematocides i.e. as foliar insecticides and soil insecticides or nematocides.

EXAMPLE 42

The organophosphorus compounds of this invention were tested as pesticides according to the following procedures:

A. Tobacco Budworm Diet Test

Test formulations were prepared at 6000 ppm (parts per million) by dissolving 0.6 g of the test compound in 10 ml of acetone and adding 4 drops of a suitable wetting agent. This solution was then diluted to 100 ml with water to give a 6000 ppm suspension. Two-tenths ml of the diluted formulation was pipetted onto the surface of 5 g of a synthetic diet mixture held in partially filled cells of a plastic jelly tray. Five cells were treated with the chemical dilution in this manner.

Following treatment, a third instar larva of the tobacco budworm, *Heliothis virescens*, was placed in each cell. At the end of one and two weeks, trays were examined and the percent control was determined.

B. Aphid Contact Test

Test formulations were prepared as in (A) above. An aliquot of the 6000 ppm suspension was further diluted with water to 1000 ppm concentration of the compound. Barley plants were infested with corn leaf aphids, *Rhopalosiphum maidis*, two days prior to treatment. Two pots were treated with each formulation by spraying with a spray atomizer. Five days after treatment, the percent control was estimated based on the reduction of the population density as compared to untreated control plants.

C. Boll Weevil Test

Test formulations were prepared at 1000 ppm as in (B). Two cotton seedlings plants were treated with each formulation by spraying with a spray atomizer. Five adult boll weevils, *Anthonomous grandis*, were placed on plants in each pot one day following treatment. The surviving weevils were counted after five days to determine the percent control.

D. Southern Corn Rootworm Pouch Test

Test formulations were prepared at 1000 ppm as in (B). Five ml of the dilution is pipetted onto a paper towel, inserted into a Ziploc plastic bag. Two corn seedlings are also soaked in the chemical preparation and placed in the plastic bag. Bags are held for 18 hours before being loaded with 5 corn rootworm, *Diabrotica undecimpunctata*, larvae. After six days, the number of live larvae are noted and the percent control is calculated.

E. Nematode Soil Test

The Southern root-knot nematode, *Meloidogyne incognita*, is reared in sandy culture soil using tomato as a host plant. Roots from culture plants are ground in a Waring blender. Ground roots and culture soil are mixed with equal parts of uninfested soil and the mixture is placed in pots. Test formulations were prepared at 1000 ppm as in (B). Twenty-five ml of the dilution is drenched per pot, giving a resultant soil concentration of 50 ppm. One day after treatment, two tomato seedlings are planted in each pot. Twelve days after planting, soil is washed from roots and treatments are evaluated by comparing the number of knots on plants roots from treated soil to those from the untreated nematode-infested control.

The results of the described tests are set forth in TABLE IV wherein the compound numbers correspond to those in Examples 1 to 4 and TABLES I–III.

TABLE IV
PYRIMIDINYL ORGANOPHOSPHORUS COMPOUNDS AS INSECTICIDES AND NEMATOCIDES

| | % CONTROL | | | | |
|---|---|---|---|---|---|
| EXAMPLE NO. | CORN LEAF APHID 1000 PPM | BOLL WEEVIL 1000 PPM | SOUTHERN CORN ROOTWORM 1000 PPM | TOBACCO BUDWORM 6000 PPM | ROOT KNOT NEMATODE 50 PPM |
| 1 | 100 | 0 | 100 | 0 | 100 |
| 3 | 40 | 90 | 100 | 100 | 100 |
| 4 | 20 | 68 | 75 | 0 | 65 |
| 13 | 20 | 80 | 100 | 0 | 90 |
| 14 | 0 | 20 | 0 | 0 | 0 |
| 15 | 100 | 82 | 100 | 0 | 100 |
| 16 | 100 | 100 | 100 | 0 | 80 |
| 17 | 0 | 100 | 100 | 0 | 100 |
| 18 | 30 | 100 | 100 | 0 | 0 |
| 19 | 30 | 16 | 20 | 0 | 0 |
| 20 | 0 | 47 | 53 | 0 | 0 |
| 21 | 0 | 20 | 100 | 0 | 50 |
| 22 | 0 | 7 | 40 | 53 | 0 |
| 23 | 75 | 7 | 20 | 29 | 0 |
| 24 | 80 | 20 | 20 | 53 | 0 |
| 25 | 100 | 55 | 78 | 37 | 80 |
| 26 | 20 | 58 | 38 | 0 | 85 |
| 27 | 0 | 26 | 58 | 20 | 0 |
| 28 | 0 | 0 | 100 | 79 | 50 |
| 29 | 15 | 0 | 100 | 77 | 75 |
| 30 | 15 | 100 | 100 | 53 | 90 |
| 31 | 20 | 100 | 100 | 29 | 100 |
| 32 | 0 | 100 | 100 | 77 | 25 |
| 33 | 95 | 100 | 100 | 100 | 70 |
| 34 | 0 | 100 | 100 | 0 | 0 |
| 35 | 0 | 100 | 100 | 6 | 0 |
| 36 | 0 | 90 | 100 | 39 | 0 |
| 37 | 0 | 100 | 100 | 100 | 100 |
| 38 | 0 | 100 | 100 | 100 | 100 |
| 39 | 0 | 50 | 100 | 20 | 90 |
| 40 | 0 | 100 | 100 | 100 | 90 |
| 41 | 50 | 70 | 0 | 100 | 40 |
| 48 | | | | | 90 |
| 49 | | | | | 80 |

EXAMPLE 43

Southern Corn Rootworm Soil Test

In this example, test formulations of several representative compounds of the invention were prepared as follows:

Prior to treatment, two hybrid corn seed were planted in the soil. Test chemicals were prepared as a 100 ppm suspension in water. Four pots, containing 360 grams of soil each, were drenched with 40 ml of the suspension to give a resulting soil concentration of 10 ppm. One week after treatment, ten Southern corn rootworm larvae were placed in each pot. Two weeks after treatment pots were emptied and the roots washed free of soil. All surviving larvae were collected from the water and percent control was calculated. The results are shown in TABLE V.

TABLE V
SOUTHERN CORN ROOTWORM SOIL TEST

| EXAMPLE NO. | % CONTROL 10 PPM |
| --- | --- |
| 1 | 79 |
| 25 | 44 |
| 28 | 88 |
| 29 | 53 |
| 30 | 82 |
| 32 | 68 |
| 33 | 44 |
| 34 | 91 |
| 35 | 44 |
| 37 | 56 |

EXAMPLE 58

Rice Planthopper Test

Test formulations were prepared at 6000 ppm (parts per million by dissolving 0.6 g of the test compound in 10 ml of acetone and adding 4 drops of a suitable wetting agent. This solution was then diluted to 100 ml with water to give a 6000 ppm suspension. An aliquot of 6000 ppm suspension was further diluted with water to 1000 ppm concentration of the compound. Two rice seedling plants were treated with each formulation by spraying with a spray atomizer. Ten adult rice planthoppers, *Sogatodes oryzicola*, were placed on plants in each pot one day following treatment. The surviving planthoppers were counted after five days to determine the percent control.

The results are summarized in TABLE VI.

TABLE VI

| Compound of Example | Rice Planthopper % Control at 1000 ppm |
| --- | --- |
| 1 | 85 |
| 4 | 60 |
| 13 | 100 |
| 15 | 100 |
| 16 | 100 |
| 17 | 90 |
| 18 | 98 |
| 19 | 70 |
| 20 | 60 |
| 21 | 70 |
| 23 | 100 |
| 24 | 100 |
| 25 | 100 |
| 26 | 20 |
| 29 | 70 |
| 33 | 100 |
| 38 | 50 |
| 40 | 50 |
| 41 | 80 |
| 44 | 70 |
| 45 | 95 |
| 46 | 80 |
| 47 | 50 |
| 48 | 100 |
| 49 | 100 |
| 50 | 100 |
| 51 | 100 |
| 52 | 100 |
| 53 | 95 |
| 54 | 50 |
| 55 | 100 |
| 56 | 95 |
| 57 | 95 |

What is claimed is:

1. An oganophosphorus compound of the formula

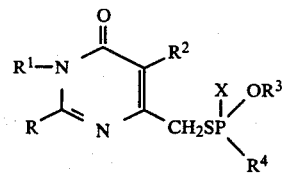

where R is $C_1$-$C_4$ alkyl; $R^1$ is hydrogen or methyl; or R and $R^1$ together are a diradical having the formula —SC(Y)=Z—, where Y is halogen, hydrogen or $C_1$-$C_2$ alkyl; and Z is nitrogen, CH, C($CH_3$) or C($C_2H_5$) with the proviso that if Y is hydrogen, Z cannot be CH; $R^2$ is hydrogen, chlorine or bromine; $R^3$ is methyl or ethyl; $R^4$ is methoxy, ethoxy, —$SCH_3$ or —$SC_2H_5$; and X is oxygen or sulfur and their hydrochlorides.

2. A compound in accordance with claim 1 wherein R is $C_1$-$C_3$ alkyl; Y is hydrogen, chlorine, bromine or $C_1$-$C_2$ alkyl with the proviso that Z is not CH if Y is hydrogen; and $R^4$ is methoxy or ethoxy.

3. A method of controlling insects or nematodes comprising applying to said insects or nematodes an insecticidally or a nematocidally effective amount of the compound of claim 1.

4. A method of controlling insects or nematodes comprising applying to said insects or nematodes an insecticidally or nematocidally effective amount of the compound of claim 2.

5. A method for controlling rice planthoppers comprising applying an insecticidally effective amount to the loci where rice planthoppers reside of a compound having the formula

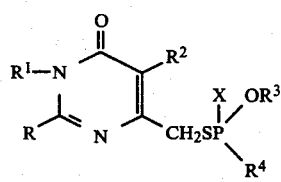

where R is $C_1$-$C_4$ alkyl or benzyl; $R^1$ is hydrogen or $C_1$-$C_3$ alkyl; or R and $R^1$ together are a diradical selected from the group consisting of —CH=CH—CH=CH—, —CH=CCl—CH=CH—, —CH=C(CH$_3$)—CH=CH— and —SC(Y)=Z— where Y is halogen, hydrogen or $C_1$-$C_2$ alkyl; and Z is nitrogen, CH, C($CH_3$) or C($C_2H_5$); $R^2$ is hydrogen or bromine; $R^3$ is methyl or ethyl; $R^4$ is methoxy, ethoxy or propylthio, with the proviso that if $R^2$ is bromine, $R^4$ is propylthio; and X is oxygen or sulfur.

* * * * *